United States Patent [19]

Walser

[11] 4,247,463
[45] Jan. 27, 1981

[54] PROCESS FOR THE PREPARATION OF IMIDAZOBENZODIAZEPINES

[75] Inventor: Armin Walser, West Caldwell, N.J.

[73] Assignee: Hoffmann-La Roche Inc., Nutley, N.J.

[21] Appl. No.: 139,533

[22] Filed: Apr. 11, 1980

Related U.S. Application Data

[62] Division of Ser. No. 60,258, Jul. 25, 1979.

[51] Int. Cl.³ .......................................... C07D 487/04
[52] U.S. Cl. .......................... 260/245.6; 260/239 BD
[58] Field of Search ...................................... 260/245.6

[56] References Cited

U.S. PATENT DOCUMENTS 4,125,726  11/1978  Walser et al. .................... 260/245.6

Primary Examiner—Alton D. Rollins
Attorney, Agent, or Firm—Jon S. Saxe; Bernard S. Leon; Frank P. Hoffman

[57] ABSTRACT

A multistep process is presented for the preparation of imidazobenzodiazepines of the formula

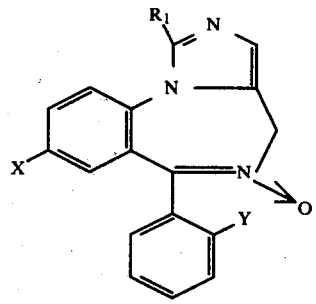

wherein X is selected from the group consisting of hydrogen, halogen, nitro and trifluoromethyl, Y is selected from the group consisting of hydrogen, halogen and trifluoromethyl and R₁ is selected from the group consisting of hydrogen, lower alkyl and aryl Also presented are novel intermediates utilized in the process.

The end products are useful as sedatives, anxiolytics, muscle relaxants and anticonvulsants.

The end products are especially useful in intravenous compositions for use in preoperative anesthesia.

1 Claim, No Drawings

PROCESS FOR THE PREPARATION OF IMIDAZOBENZODIAZEPINES

This is a division of application Ser. No. 60,258 filed July 25, 1979.

DESCRIPTION OF THE INVENTION

The present invention relates to a process to produce imidazobenzodiazepines of the formula

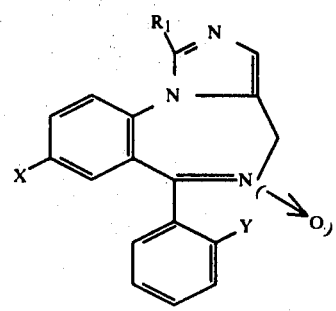

wherein X is selected from the group consisting of hydrogen, halogen, nitro and trifluoromethyl, Y is selected from the group consisting of hydrogen, halogen and trifluoromethyl and $R_1$ is selected from the group consisting of hydrogen, lower alkyl and aryl.

The imidazobenzodiazepines are useful as sedatives, anxiolytics, muscle relaxants and anticonvulsants, a description of these compounds can be found in Belgian Pat. No. 839,364 which is incorporated herein by reference.

As utilized in the present specification, the terms "halo" or "halogen" mean all four forms thereof, i.e., chlorine, bromine, iodine and fluorine, except where otherwise indicated.

The following reaction scheme sets forth the novel process.

Reaction Scheme

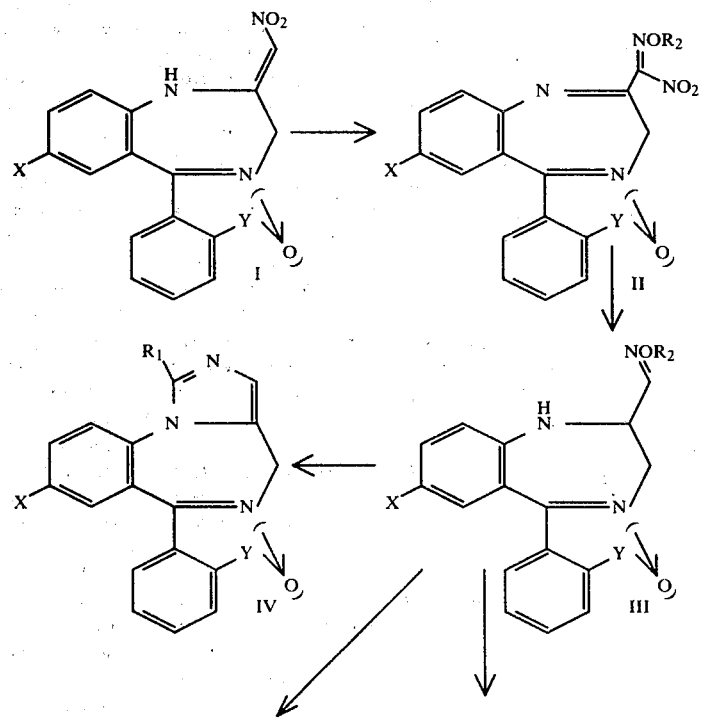

Reaction Scheme

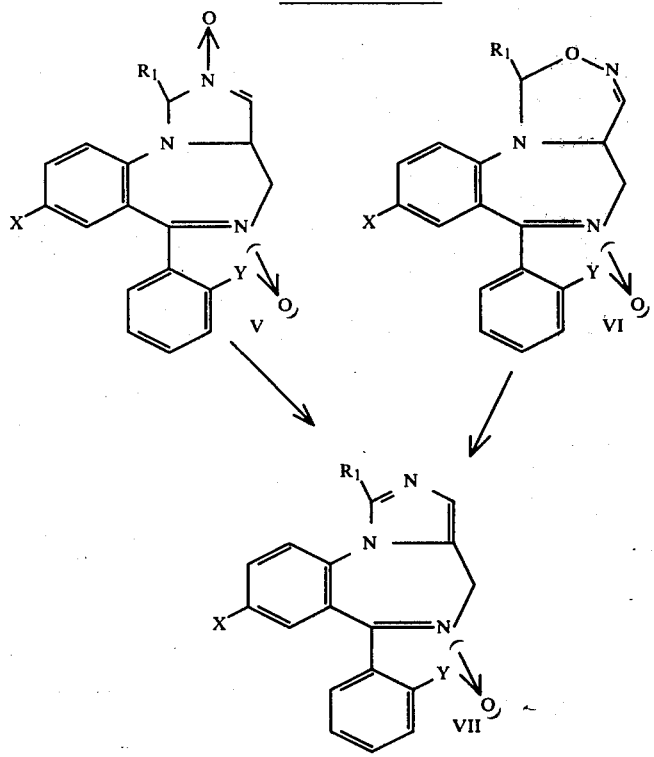

wherein X is selected from the group consisting of hydrogen, halogen, nitro and trifluoromethyl, Y is selected from the group consisting of hydrogen, halogen and trifluoromethyl, $R_1$ is selected from the group consisting of hydrogen, lower alkyl and aryl and $R_2$ is hydrogen or lower alkyl.

I→II

The nitromethylene compound of formula I is a known compoud. Methods for its preparation are described in the previously mentioned Belgian Pat. No. 839,364. This starting material is thereafter reacted with a nitrosating agent, such as, nitrosyl chloride or nitrous acid which is generated from sodium or potassium nitrite in an acetic acid solvent to provide formula II compound where $R_2=H$. As a solvent, acetic acid is preferred but mixtures of acetic acid and a $C_1$ to $C_4$ alcohol or water may also be utilized. The reaction temperature may range from about 0° C. to 50° C. with about room temperature as preferred.

Compounds of formula II where $R_2=H$ may be converted to compounds where $R_2=$ lower alkyl by reaction with diazomethane in an inert solvent, such as methylene chloride.

II→III

The compound of formula II is thereafter reduced by reaction with sodium borohydride. A variety of solvents may be utilized, such as, $C_1$-$C_4$ alcohols or mixtures thereof with inert hydrocarbons or chlorinated hydrocarbons, e.g., benzene, toluene, chloroform or methylene chloride, ethers or dimethylformamide. Preferred is a mixture of ethanol and tetrahydrofuran. The reaction temperature varies from about 0° C. to 50° C. with room temperature as preferred.

II→IV

The compound of formula III may be cyclized to the desired imidazobenzodiazepines of formula IV by condensation with an aliphatic or aromatic aldehyde, e.g., acetaldehyde, in the presence of an acid catalyst, such as, p-toluene sulfonic acid, acetic acid or hydrochloric or sulfuric acid. Suitable solvents include $C_1$ to $C_4$ alcohols, inert hydrocarbons and chlorinated hydrocarbons as mentioned earlier, high boiling ethers, acetic acid and propionic acid. The reaction temperature may vary from about room temperature to 120° C. with the boiling point of the chosen solvent as preferred.

III→V and VI

The compound of formula III where $R_2=H$ is thereafter reacted with formaldehyde and pivalic acid with 1,2 dichloroethane as solvent to form the oxadiazine of formula V and the imidazoline N-oxide of formula VI. Reaction temperature is about reflux temperature.

The oxadiazine (V) can then be converted to the imidazobenzodiazepine of formula VII by acid catalysis, under more vigorous conditions i.e., reaction with acetic acid at reflux temperatures. The imidazoline N-oxide (VI) can be converted to the imidazobenzodiazepine (VII) by either acid catalysis as above or base catalysis i.e., reaction with sodium methoxide in methanol at reflux temperature.

The novel intermediates of formulas V and VI also exhibit pharmacological activity as sedatives and anxiolytics.

As utilized herein the term "lower alkyl" means both straight and branched chain ($C_1$-$C_7$) carbon-hydrogen radicals, preferably $C_1$-$C_4$ carbon-hydrogen radicals, such as, methyl, ethyl, propyl, isopropyl and the like.

By the term "aryl" is meant a substituted or unsubstituted monocyclic aromatic moiety, such as, phenyl, chlorophenyl, tolyl and the like. Substituents on the phenyl ring include halogen and nitro.

EXAMPLE 1

7-Chloro-5-(2-fluorophenyl)-N-hydroxy-α-nitro-3H-1,4-benzodiazepine-2-methanimine Sodium nitrite, 5 g (0.072 mole), was added in portions over a period of 5 min to a solution of 20 g (0.06 mole) of 7-chloro-1,3-dihydro-5-(2-fluorophenyl)-2-nitromethylene-2H-1,4-benzodiazepine* in 100 ml of glacial acetic acid. Following the addition, the reaction mixture was stirred at room temperature for 15 min. The product, which crystallized partially during this period, was further precipitated by slow addition of 50 ml of water and collected by filtration. The crystals were washed with water, sucked dry and washed with methanol/ether to leave light yellow product. The filtrate was diluted with water and extracted with methylene chloride. The extracts were washed with water, dried and evaporated. Crystallization of the residue from methylene chloride/hexane yielded additional product. The analytical sample was recrystallized from ether to give pale yellow crystals with mp 220°–230° C. dec.

*Walser et al., *J. Org. Chem.* 43, 936 (1978)

EXAMPLE 2

7-Chloro-5-(2-fluorophenyl)-N-hydroxy-α-nitro-3H-1,4-benzodiazepine-2-methanimine 4-oxide 7-Chloro-5-(2-fluorophenyl)-1,3-dihydro-2-nitromethylene-2H-1,4-benzodiazepine-4-oxide* 7 g (0.02 mole), was dissolved by heating in 250 ml of glacial acetic acid. The solution was cooled with tap water and when the temperature reached 70° C. the addition of 1.9 g (0.0275 mole) of sodium nitrite was started. The sodium nitrite was added over a period of 10 min while cooling was continued. Following the addition, the mixture was stirred for 1½ hr at room temperature, diluted with water and extracted with methylene chloride. The extracts were washed with water, dried over sodium sulfate and evaporated. Crystallization of the residue from ethyl acetate yielded yellow crystals. The analytical sample was recrystallized from methanol/ethyl acetate to give yellow crystals with undefined mp. The compound decomposes without prior melting.

*Fryer et al., *J. Heterocyclic Chemistry* 13, 433 (1976)

EXAMPLE 3

7-Chloro-2,3-dihydro-5-(2-fluorophenyl)-1H-1,4-benzodiazepine-2-carboxaldoxime Sodium borohydride, 1.6 g (0.042 mole) was added in two portions at 15 min intervals to a suspension of 3.6 g (0.01 mole) of 7-chloro-5-(2-fluorophenyl)-N-hydroxy-α-nitro-3H-1,4-benzodiazepine-2-methanimine in 50 ml of ethanol. After stirring for 4 hr at room temperature the reaction mixture was partitioned between methylene chloride and sodium bicarbonate solution. The organic phase was dried and evaporated. Crystallization of the residue from ether yielded yellowish crystals with mp 185°–190° C. Recrystallization from methylene chloride/ethyl acetate raised the mp to 193°–195° C.

EXAMPLE 4

7-Chloro-2,3-dihydro-5-(2-fluorophenyl)-1H-1,4-benzodiazepine-2-carboxaldoxime-4-oxide Sodium borohydride, 0.5 g (13 mmole) was added to a solution of 1.9 g (5 mmole) of 7-chloro-5-(2-fluorophenyl)-N-hydroxy-α-oxide in 50 ml of ethanol and 25 ml of tetrahydrofuran. The mixture was stirred at room temperature for 2½ hr, evaporated partially under reduced pressure and partitioned between methylene chloride and sodium bicarbonate solution. The organic phase was dried and evaporated and the residue was crystallized from ether to yield yellow crystals with mp 178°–181° C. dec. The analytical sample was recrystallized from methanol/ethyl acetate and had mp 184°–186° C. dec.

EXAMPLE 5

8-Chloro-6-(2-fluorophenyl)-1-methyl-4H-imidazo[1,5-a][1,4]benzodiazepine maleate A mixture of 0.32 g (1 mmole) of 7-chloro-2,3-dihydro-5-(2-fluorophenyl)-1H-1,4-benzodiazepine-2-carboxaldoxime, 15 ml of glacial acetic acid and 0.3 ml of acetaldehyde was heated to reflux for 10 min. The acetic acid was evaporated under reduced pressure and the residue was partitioned between methylene chloride and dilute aqueous ammonia. The organic phase was dried and evaporated and the brown residue was chromatographed over 7 g of silica gel using 5% (v/v) of ethanol in methylene chloride. The fractions containing product were combined and evaporated. The base was dissolved in 2-propanol and the solution was treated with 0.11 g (0.95 mmole) of maleic acid. The maleate was crystallized by addition of ether. The tan crystals were collected and dried at 90° C. under vacuum with mp 148°–151° C.

EXAMPLE 6

8-Chloro-6-(2-fluorophenyl)-1-methyl-4H-imidazo[1,5-a][1,4]benzodiazepine 5-oxide A mixture of 0.34 g (1 mmole) of 7-chloro-2,3-dihydro-5-(2-fluorophenyl)-1H-1,4-benzodiazepine-2-carboxaldoxime 4-oxide, 0.3 ml of acetaldehyde and 15 ml of glacial acetic acid was heated to reflux for 10 min. The reaction was worked up as above and the product was isolated by chromatography on 7 g of silica gel using 5% (v/v) of ethanol in methylene chloride as eluent. The fractions containing the desired product were combined and evaporated. Crystallization of the residue from ethyl acetate/hexane gave product which had mp 243°–246° C. dec after recrystallization from methylene chloride/ether.

EXAMPLE 7

8-Chloro-6-(2-fluorophenyl)-4H-imidazo[1,5-a][1,4]benzodiazepine (A) A mixture of 0.2 g (0.64 mmole) of 7-chloro-2,3-dihydro-5-(2-fluorophenyl)-1H-1,4-benzodiazepine-2-carboxaldoxime, 0.1 g (3.3 mmole) of paraformaldehyde and 5 ml of glacial acetic acid was heated to reflux for 5 min. The reaction mixture was worked up as described in the previous example and the crude product was chromatographed over 5 g of silica gel using 5% (v/v) of ethanol in methylene chloride. Crystallization of the combined fractions from ether/hexane yielded tan crystals. Recrystallization from ethyl acetate/hexane gave product with mp 150°–151° C.

(B) A solution of 0.15 g of 9-chloro-7-(2-fluorophenyl)-4a,5-dihydro-1H-[1,2,5]oxadiazino[5,4-a][1,4]benzodiazepine in 5 ml of glacial acetic acid was heated to reflux for 15 min. The solvent was evaporated under reduced pressure and the residue was partitioned between methylene chloride and saturated sodium bicarbonate solution. The organic phase was dried and evaporated. Chromatography of the residue on 5 g of silica gel using 5% (v/v) of ethanol in methylene chloride and crystallization from ether containing a few drops of 2-propanol yielded product with mp 148°–151° C.

(C) A solution of 50 mg of 8-chloro-6-(2-fluorophenyl)-3a,4-dihydro-1H-imidazo[1,5-a][1,4]benzodiazepine 2-oxide in 3 ml of glacial acetic acid was heated to reflux for 15 min. The mixture was worked up as described above and the product was isolated by chromatography over 3 g of silica gel using 5% (v/v) of ethanol in methylene chloride. Crystallization from ether yielded product with mp 149°–151° C.

(D) A solution of 50 mg of 8-chloro-6-(2-fluorophenyl)-3a,4-dihydro-1H-imidazo[1,5-a][1,4]benzodiazepine 2-oxide in 3 ml of methanol containing 25 mg of potassium t-butoxide was heated to reflux for 10 min. The mixture was evaporated partially and the residue was partitioned between methylene chloride and sodium bicarbonate solution. The organic phase was dried and evaporated. Crystallization of the residue from ether yielded product with mp 148°–151° C.

EXAMPLE 8

8-Chloro-6-(2-fluorophenyl)-1-isopropyl-4H-imidazo[1,5-a][1,4]benzodiazepine

The end product was similarly prepared by condensation of 7-chloro-2,3-dihydro-5-(2-fluorophenyl)-1H-1,4-benzodiazepine-2-carboxaldoxime with isobutyraldehyde. The analytical sample was recrystallized from ether/hexane, mp 168°–169° C.

EXAMPLE 9

8-Chloro-1-ethyl-6-(2-fluorophenyl)-4H-imidazo[1,5-a][1,4]benzodiazepine

The end product was obtained by reaction of 7-chloro-2,3-dihydro-5-(2-fluorophenyl)-1H-1,4-benzodiazepine-2-carboxaldoxime with propionaldehyde. Isolation by chromatography and crystallization from ether gave end product with mp 143°–145° C. The base was converted to a maleate salt which crystallized from ethanol/ether and had mp 163°–165° C.

EXAMPLE 10

8-Chloro-6-(2-fluorophenyl)-1-phenyl-4H-imidazo[1,5-a][1,4]benzodiazepine

The end product was formed by condensation of 7-chloro-2,3-dihydro-5-(2-fluorophenyl)-1H-1,4-benzodiazepine-2-carboxaldoxime with benzaldehyde. The product had mp 241°–243° C. and the mix mp with previously synthesized material was undepressed.

EXAMPLE 11

9-Chloro-7-(2-fluorophenyl)-4a,5-dihydro-1H-[1,2,5]oxadiazino[5,4-a][1,4]benzodiazepine and 8-chloro-6-(2-fluorophenyl)-3a,4-dihydro-1H-imidazo[1,5-a][1,4]benzodiazepine 2-oxide A mixture of 3.2 g (0.01 mole) of 7-chloro-5-(2-fluorophenyl)-2,3-dihydro-1H-1,4-benzodiazepine-2-carboxaldoxime, 1.0 g of paraformaldehyde, 1.0 g of pivalic acid and 150 ml of 1,2-dichloroethane was heated to reflux for 30 min with separation of water. The reaction mixture was washed with saturated sodium bicarbonate solution, dried and evaporated. The residue was chromatographed over 60 g of silica gel using 5% (v/v) of ethanol in methylene chloride followed by 10% ethanol in methylene chloride. The fractions containing the less polar oxadiazine were combined and evaporated. Crystallization from ether yielded the 9-chloro-7-(2-fluorophenyl)-4a,5-dihydro-1H-[1,2,5]oxadiazino[5,4-a][1,4]benzodiazepine which was recrystallized from ethyl acetate/methanol for analysis to give colorless needles with mp 230°–233° C.

The fractions containing the more polar component were combined and evaporated and the residue was crystallized from ether to yield the N-oxide with mp 182°–184° C.

EXAMPLE 12

8-Chloro-6-(2-fluorophenyl)-1-methyl-4H-imidazo[1,5-a][1,4-]benzodiazepine 5-oxide A mixture of 0.5 g of 7-chloro-5-(2-fluorophenyl)-N-methoxy-α-nitro-3H-1,4-benzodiazepine-2-methanimine 4-oxide, 10 ml of ethanol, 5 ml of tetrahydrofuran and 0.4 g of sodium borohydride was stirred at ambient temperature for 1 hr. After partitioning between methylene chloride and aqueous sodium bicarbonate solution, the organic phase was dried and evaporated. Chromatography of the residue over 7 g of silica gel yielded 7-chloro-5-(2-fluorophenyl)-2,3-dihydro-N-methoxy-1H-1,4-benzodiazepine-2-methanimine 4-oxide as light yellow resin.

This material was dissolved in 5 ml of glacial acetic acid. Following the addition of 0.25 ml of acetaldehyde the mixture was heated to reflux for 15 min. The dark solution was poured on ice, made alkaline with ammonia and extracted with methylene chloride. The extracts were dried and evaporated. The residue was chromatographed over 6 g of SiO$_2$ using 3% (v/v) of ethanol in methylene chloride for elution.

The fractions containing the desired product were combined and evaporated. Crystallization of the residue from ethyl acetate gave crystals with mp 235°–240° C. dec. after recrystallization from methanol/ethyl acetate.

EXAMPLE 13

7-Chloro-5-(2-fluorophenyl)-N-methoxy-α-nitro-3H-1,4-benzodiazepine-2-methanimine 4-oxide A solution of diazomethane in ether was added to a suspension of 3.8 g (0.01 mol) of 7-chloro-5-(2-fluorophenyl)-N-hydroy-α-nitro-3H-1,4-benzodiazepine-2-methanimine 4-oxide in 200 ml of methylene chloride. The mixture was stirred for 1 hr at room temperature whereby a clear solution resulted. The excess diazomethane was destroyed by addition of acetic acid. The reaction mixture was washed with aqueous sodium bicarbonate solution, dried over sodium sulfate and evaporated. Crystallization of the residue from ether yielded yellow crystals. The analytical sample was recrystallized from ether, mp 207°–209°.

What is claimed:

1. A process to produce a compound of the formula

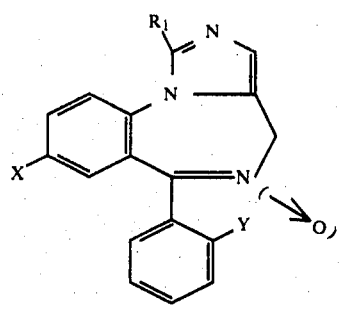

wherein X is selected from the group consisting of hydrogen, halogen, nitro and trifluoromethyl, Y is selected from the group consisting of hydrogen, halogen and trifluoromethyl and $R_1$ is selected from the group consisting of hydrogen, lower alkyl and aryl which comprises (A) reacting a compound of the formula

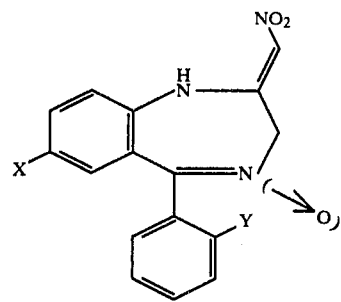

wherein X and Y are as above with a nitrosating agent (B) reacting the product of (A) with sodium borohydride (C) reacting the product of (B) with an aliphatic or aromatic aldehyde in the presence of an acid catalyst.

* * * * *